US00PP31479P2

(12) United States Plant Patent
Lannes

(10) Patent No.: US PP31,479 P2
(45) Date of Patent: Feb. 25, 2020

(54) ***HIBISCUS* PLANT NAMED 'LANCHIPPEWA'**

(50) Latin Name: *Hibiscus rosa-sinensis*
Varietal Denomination: Lanchippewa

(71) Applicant: D.H.M. INNOVATION, Malause (FR)

(72) Inventor: Robert M. Lannes, Malause (FR)

(73) Assignee: D.H.M. INNOVATION, Malause (FR)

( * ) Notice: Subject to any disclaimer, the term of this patent is extended or adjusted under 35 U.S.C. 154(b) by 0 days.

(21) Appl. No.: 16/501,418

(22) Filed: Apr. 10, 2019

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ..... A01H 5/02; A01H 6/60
See application file for complete search history.

*Primary Examiner* — Annette H Para
(74) *Attorney, Agent, or Firm* — Penny J. Aguirre

(57) ABSTRACT

A new cultivar of *Hibiscus* plant named 'Lanchippewa' that is characterized by its uniform flowers that are bright orange in color with pink and yellow veins, its floriferous habit with flowers that last for 2 to 3 days, its early blooming and freely flowering habit, its compact and self-branching plant habit, and its foliage that is resistant to pathogens common to *Hibiscus*, including *Pseudomonas* sp., *Phythium* sp., and *Phytophthora* sp.

2 Drawing Sheets

Botanical classification: *Hibiscus rosa-sinensis.*
Cultivar designation: 'Lanchippewa'.

CROSS REFERENCE TO A RELATED APPLICATIONS

This application is related U.S. Plant Patents for plants derived from the same breeding program that are entitled *Hibiscus* Plant Named 'Lanlampasas' (U.S. Plant Pat. No. 25,660) and *Hibiscus* Plant Named 'Lanred' (U.S. Plant Pat. No. 25,678).

BACKGROUND OF THE INVENTION

The present invention relates to a new and distinct cultivar of *Hibiscus rosa-sinensis* named 'Lanchippewa' and will be referred to hereafter by its cultivar name, 'Lanouachita'. 'Lanchippewa' is a new cultivar of tropical *Hibiscus* grown for use as a landscape and container plant.

The new cultivar was developed through an ongoing breeding program conducted by the Inventor in Malause, France. The objectives of the breeding program are to develop new cultivars of *Hibiscus* that exhibit brightly colored unique flowers, self-branching, high flower bud counts, and compact plant habits.

'Lanchippewa' arose from a cross made by the Inventor in July of 2011 between an unnamed plant of *Hibiscus rosa-sinensis* from the breeding program, reference no. si 0378-1, as the female parent and *Hibiscus rosa-sinensis* 'Lanlampasas' as the male parent. 'Lanchippewa' was selected as a single unique plant from the resulting seedlings in June of 2012.

Asexual propagation of the new cultivar was first accomplished by the Inventor by stem cuttings in July of 2014 in Malause, France. Asexual propagation by stem cuttings has determined that the characteristics of the new cultivar are stable and are reproduced true to type in successive generations.

SUMMARY OF THE INVENTION

The following traits have been repeatedly observed and represent the characteristics the new cultivar. These attributes in combination distinguish 'Lanchippewa' as a new and distinct cultivar of *Hibiscus.*

1. 'Lanchippewa' exhibits uniform flowers that are bright orange in color with pink and yellow veins.
2. 'Lanchippewa' exhibits a floriferous habit with flowers that last for 2 to 3 days.
3. 'Lanchippewa' exhibits an early blooming and freely flowering habit.
4. 'Lanchippewa' exhibits a compact and self-branching plant habit.
5. 'Lanchippewa' exhibits foliage that is resistant to pathogens common to *Hibiscus*, including *Pseudomonas* sp., *Phythium* sp., and *Phytophthora* sp.

The female parent of 'Lanchippewa' differs from 'Lanchippewa' in having a shorter blooming period, smaller flowers with a poor flower bud count, and less branching. The male parent of 'Lanchippewa', 'Lanlampasas', is similar to 'Lanchippewa' in being floriferous all season. 'Lanlampasas' differs from 'Lanchippewa' in having flowers that are light orange in color with a large pink center with softer and larger petals, and in having a less compact plant habit. 'Lanchippewa' can also be compared to in the *Hibiscus* cultivar 'Lanred' (not patented). 'Lanred' is similar to 'Lanchippewa' in having glossy foliage that tolerates heat and sun well and in having similar mid-sized flowers. 'Lanred' differs from 'Lanchippewa' in having flowers that do not open completely with curled petals that are orange/red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of the new *Hibiscus*. The photographs were taken of a 15-month-old plant of 'Lanchippewa' as grown in a two-gallon container in Malause, France.

The photograph in FIG. 1 provides a side view of 'Lanchippewa' in bloom.

Figure 1:
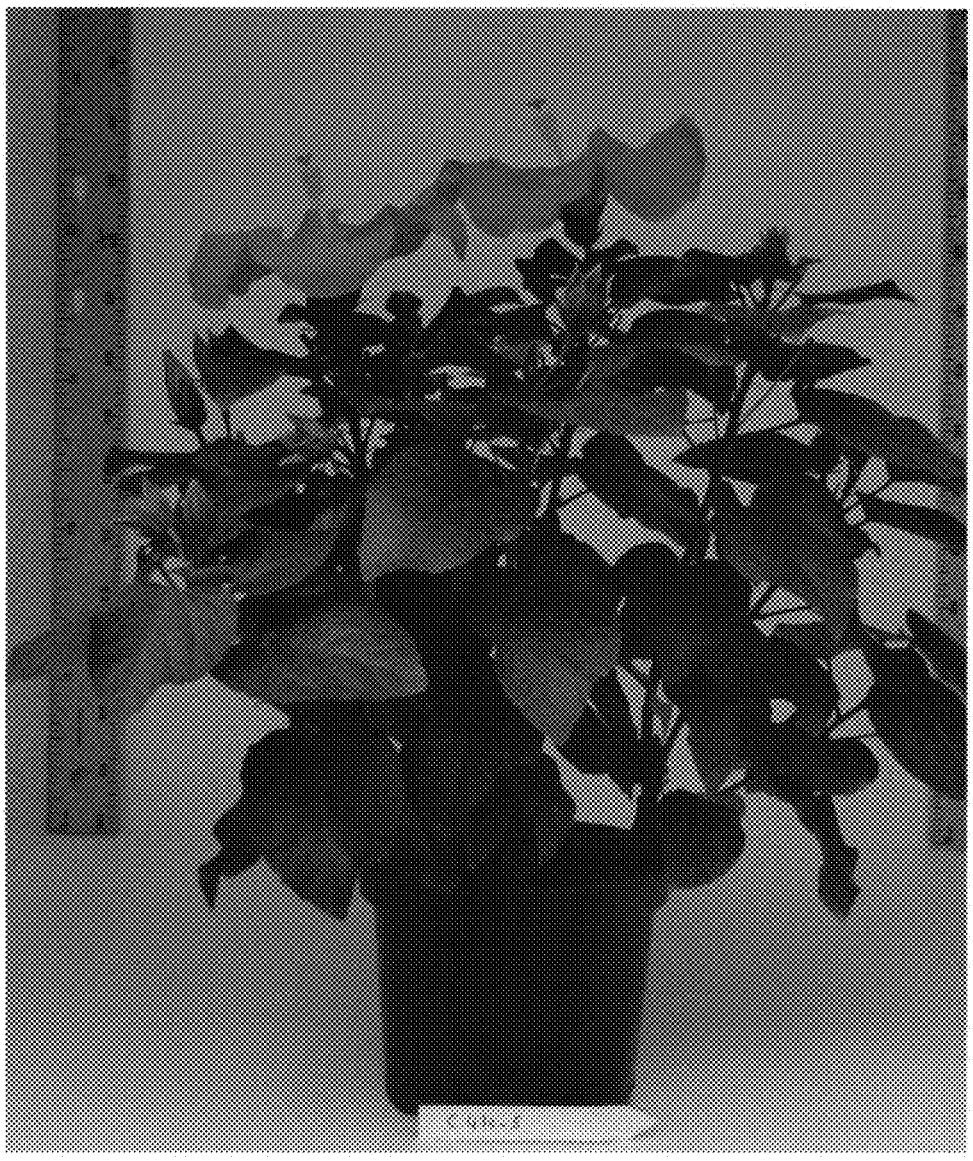
Figure 2:
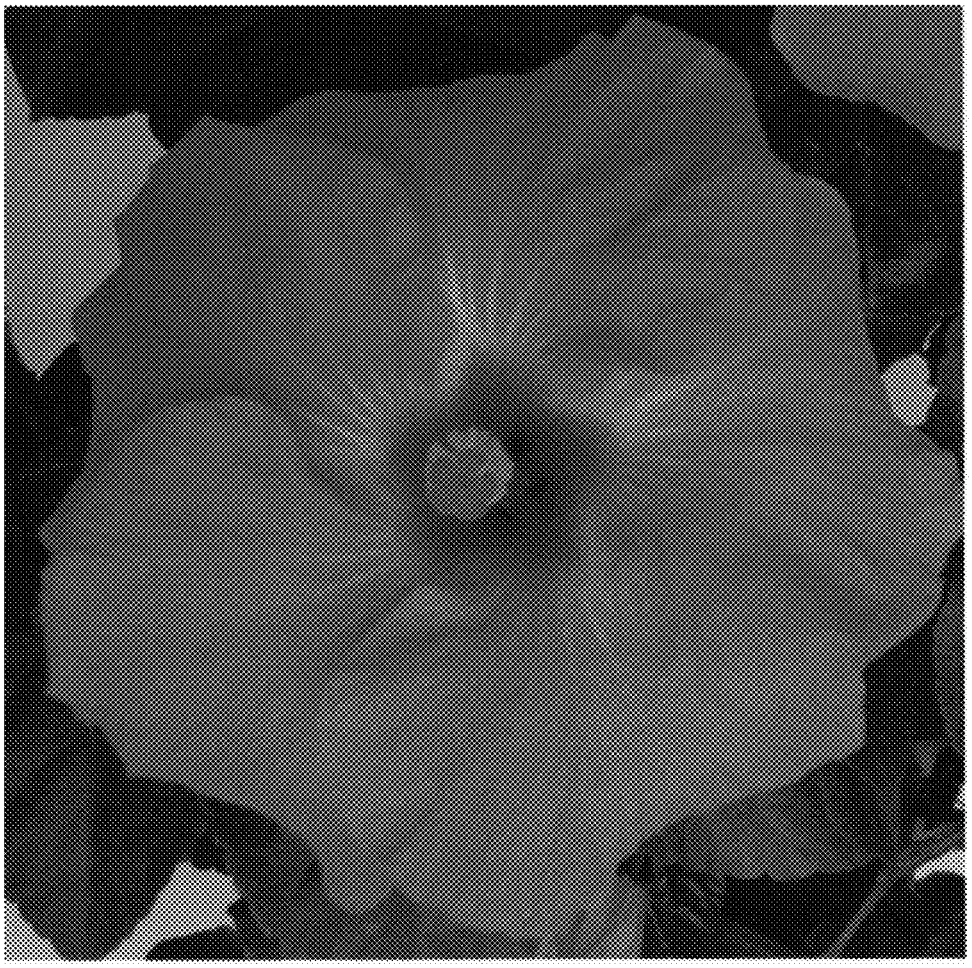

The photograph in FIG. 2 provides a close-up view of a flower of 'Lanchippewa'.

The colors in the photographs are as close as possible with the photographic and printing technology utilized and the color values cited in the Detailed Botanical Description accurately describe the colors of the new *Hibiscus*.

DETAILED BOTANICAL DESCRIPTION OF THE PLANT

The following is a detailed description of 15-month-old plants of the new cultivar as grown in two-gallon containers in a greenhouse in Grand Saline, Tex. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

- *Blooming period*.—Continuously producing in warm temperatures 55° F. to 90° F. in France.
- *Plant type*.—Tropical evergreen shrub.
- *Plant habit*.—Moderately upright, compact and self-branching plant habit.
- *Height and spread*.—An average of 37 cm in height and 45 cm in spread as grown in a one gallon container, reaching an average of 1.2 m in height and 1.5 m in width in the landscape.
- *Hardiness*.—Tropical; at least in U.S.D.A. Zones 9 to 10.
- *Diseases*.—Resistance to pathogens common to *Hibiscus*, including *Pseudomonas* sp., *Phythium* sp., and *Phytophthora* sp.
- *Root description*.—Fibrous roots, 161A in color.
- *Propagation*.—Stem cuttings.
- *Root development*.—Roots initiate in about 20 days and develop as a young plant in about 2 months.
- *Growth rate*.—Moderate.

Stem description:

- *Shape*.—Slightly oval.
- *Stem color*.—New growth; 146A, mature wood; 199D with striations of 197A.
- *Stem size*.—Main stem; 10 cm in length, 1.5 cm in diameter, lateral branches; average of 35 cm in length and 5 mm in width.
- *Stem surface*.—New growth; sparsely pubescent, very shiny, mature wood; finely striated and rugose.
- *Stem aspect*.—Held in multiple angles.
- *Stem strength*.—Strong.
- *Branching*.—An average of 10 lateral branches.
- *Internode*.—Ranges between 1 and 4 cm.
- *Stipules*.—2 per upper leaf node, linear to narrowly lanceolate in shape, an average of 6 mm in length and 0.5 mm in width, glabrous surface, acuminate apex, truncate base, 144A in color.

Foliage description:

- *Leaf shape*.—Deltoid to cordate.
- *Leaf division*.—Simple.
- *Leaf base*.—Truncate.
- *Leaf apex*.—Acute to bluntly acute.
- *Leaf venation*.—Pinnate, matches leaf surfaces.
- *Leaf margins*.—Serrate and slightly wavy, tips of serration have a small mucronate tip.
- *Leaf attachment*.—Petiolate.
- *Leaf arrangement*.—Alternate.
- *Leaf orientation*.—Slightly upward to horizontal to slightly downward to petiole.
- *Leaf aspect*.—Primarily flat with slightly wavy margins.
- *Leaf surface*.—Upper surface glabrous and glossy, lower surface glabrous and matte.
- *Leaf color*.—Young leaves upper and lower surface; 144A, mature leaves upper surface; 147A, mature leaves lower surface; 147B.
- *Leaf size*.—An average of 10 cm in length and 8 cm in width when mature.
- *Leaf quantity*.—An average of 16 per branch.
- *Petioles*.—An average of 3.5 cm in length and 2 mm in diameter, 145A in color, finely pubescent surface.

Flower description:

- *Inflorescence type*.—Flowers are solitary from upper leaf axils.
- *Lastingness of flowers*.—An average of 2 to 3 days, self cleaning.
- *Flower size*.—An average of 6 cm in depth and 15 cm in diameter.
- *Flower fragrance*.—None.
- *Flower shape*.—Rotate.
- *Flower number*.—Average of 5, produced at one time, continuously produces throughout the summer.
- *Flower aspect*.—Outward to slightly upright.
- *Flower bud*.—Elliptic in shape, an average of 4 cm in length and 2 cm in width, a blend of 35A and 18A in color with sepal portion 144A, glabrous surface.
- *Petals*.—5, 5% fused, 10% overlapping, oblanceolate in shape, an average of 8.5 cm in length and 6 cm in width, slightly serrate and wavy margins, rounded apex, base is cuneate slightly oblique and adnate to base of style re-curved, lower surface is glossy, upper surface; satiny and waxy near the base (throat), color upper surface when opening and fully open; tips a blend of N30A and 42A, mid-section N30A and N30B, base 60A, flushing up and becoming a blend of 67A and 73C where the color changes at the mid-section, center veins faintly flushed with 159A, color lower surface when opening and when fully open; a blend of 37A, 38A, with flushes of 18A, veins slightly flushed with 18B, base is 63C.
- *Calyx*.—Campanulate in shape, average of 3.5 cm in length and 1 cm in diameter.
- *Epicalyx*.—Comprised of 6 bracts held upright surrounding sepals, lanceolate in shape, apiculate apex, truncate base, average of 2 cm in length and 5 mm in width, color of both surfaces is a blend of 147A and 146A, base 145A, both surfaces are glabrous and dull.

*Sepals*.—5, base 50% fused, an average of 3 cm in length and 1 cm in width, color of both surfaces is a blend of 143B, 143A and 141A, outer surface is puberulent and inner surface is glossy, acute apex, truncate base.

*Peduncles*.—An average of 6 cm in length and 4 mm in diameter, strong, average angle upright to outward, 144A in color, glabrous and glossy surface.

*Pedicels*.—Not present, flowers are solitary from terminal leaf axils.

*Receptacle*.—7 mm in diameter, 144A in color, glabrous and glossy surface.

Reproductive organs:

*Gynoecium*.—Pistil; 1, 8 cm in length, stigmas; 5, irregular triangular in shape, 5 mm in diameter, 2 mm in depth, surface densely covered with short fuzzy hairs, color N30A, style arms; 8 mm in length, 1 mm in width, 18D in color, surface is glabrous and glossy, style; average of 5.5 cm in length and 4 mm in width, smooth and glossy surface, color a blend of 38B, 39A and N45A at the base, ovary; orbicular in shape with round apex, 1.5 cm in length, 5 mm width, 150B in color.

*Androecium*.—Stamens; average of 50, 4 mm in length, stamens are clustered and implanted into upper portion of style, anthers; dorsifixed and curled in shape, 2 mm in diameter, 2 mm in depth, color 10B, filament; 2 mm in length, color 38A, pollen; abundant in quantity and 23A in color.

*Fruit/seeds*.—None observed to date.

It is claimed:

1. A new and distinct cultivar of *Hibiscus* plant named 'Lanchippewa' as herein illustrated and described.

* * * * *